United States Patent [19]

Caspari

[11] 4,038,197
[45] July 26, 1977

[54] S-TRIAZINE DERIVATIVES AS MULTI-FUNCTIONAL ADDITIVES FOR LUBRICATING OILS

[75] Inventor: Gunter Caspari, Wheaton, Ill.

[73] Assignee: Standard Oil Company (Indiana), Chicago, Ill.

[21] Appl. No.: 625,015

[22] Filed: Oct. 20, 1975

[51] Int. Cl.² .............................................. C10M 1/48
[52] U.S. Cl. ........................... 252/46.7; 252/47;
  252/47.5; 252/49.8; 252/49.9; 260/248 CS
[58] Field of Search ................ 252/46.7, 47, 47.5,
  252/49.9, 51, 49.8

[56] References Cited
U.S. PATENT DOCUMENTS

| | | | |
|---|---|---|---|
| 2,706,194 | 4/1955 | Morris et al. | 252/49.9 X |
| 3,156,690 | 11/1964 | Dexter et al. | 252/47 X |
| 3,198,797 | 8/1965 | Dexter et al. | 252/51 X |
| 3,328,399 | 6/1967 | Prill | 252/51 X |
| 3,410,809 | 11/1968 | Johns | 252/49.9 X |
| 3,523,118 | 8/1970 | Emerson et al. | 252/51 X |
| 3,623,985 | 11/1971 | Hendrickson | 252/46.7 X |
| 3,642,630 | 2/1972 | MacPhail | 252/47 X |
| 3,785,977 | 1/1974 | Flowerday et al. | 252/47 X |
| 3,819,572 | 6/1974 | Dexter et al. | 252/47 X |
| 3,849,319 | 11/1974 | Nebzydoski | 252/47 X |

*Primary Examiner*—Delbert E. Gantz
*Assistant Examiner*—Andrew H. Metz
*Attorney, Agent, or Firm*—Frank J. Sroka; Arthur G. Gilkes; William T. McClain

[57] ABSTRACT

Disclosed are lubricating oil compositions containing from about 0.01 weight percent to about 5 weight percent of oil-soluble multifunctional additive having the general formula

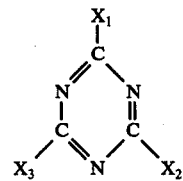

where
a. $X_1$ is —S—CS—OR, —S—CS—$NR_2$, —S—PS—$(OR)_2$, or —O—$P(OR)_2$, and $X_2$ and $X_3$ are chlorine, bromine, —S—CS—OR, —S—CS—$NR_2$, —S—PS—$(OR)_2$, —$OP(OR)_2$, or R; or
b. $X_1$ is —S—CS—OR, —S—CS—$NR_2$, —S—PS—$(OR)_2$, or —O—P—$(OR)_2$, and $X_2$ and $X_3$ are chlorine, bromine, —S—CS—OR, —S—CS—$NR_2$, —S—PS—$(OR)_2$, —O—P—$(OR)_2$ or —HN—R′ where R comprises hydrocarbyl groups or chlorine, bromine or hydroxy substituted hydrocarbyl; and R′ comprises hydrocarbyl, or hydroxy, amine or amide substituted hydrocarbyl. The lubricating oil compositions have improved extreme pressure, dispersancy or anti-oxidant properties.

26 Claims, No Drawings

S-TRIAZINE DERIVATIVES AS MULTI-FUNCTIONAL ADDITIVES FOR LUBRICATING OILS

BACKGROUND

This invention relates to novel lubricating oil compositions containing oil soluble multifunctional additives.

It has been long recognized that additives can be used in lubricating oils to improve various properties such as dispersancy, extreme pressure, anti-oxidancy and others. Additives derived from s-triazines have been used previously in lubricating oils and gasoline. U.S. Pat. No. 3,309,345 discloses oil-soluble polymeric derivatives of s-triazines having the formula

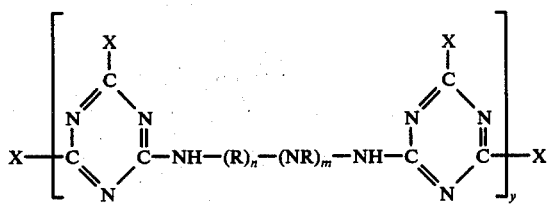

where X is a polar radical selected from the group consisting of R'O—, R'S—, R'NH—; where R is a bivalent organic radical, preferably an alkylene radical of 2 to 20 carbon atoms such as ethylene, propylene, hexylene radicals or a phenylene radical, $n$ is an integer of at least 1, R' is a hydrocarbyl radical such as alkyl or aryl radical and $m$ may be zero or 1, $y$ is an integer of from 1 to 20, preferably 2 to 10.

Another patent, U.S. Pat. No. 3,158,450, teaches the use of various triazinyl derivatives as gasoline anti-knock additives. These additives are s-triazinyl phosphonium compounds having at least one and no more than three phosphonium radicals attached to the carbon atoms of said s-triazinyl nucleus, said phosphonium radical being selected from the class consisting of

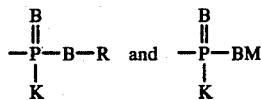

radicals, wherein B is an atom selected from the class consisting of oxygen and sulfur, R represents a radical selected from the class consisting of hydrogen, hydrocarbon radicals having no more than 20 carbon atoms therein, and derivatives of said hydrocarbon radicals having only derivative groups attached thereto selected from the class consisting of hydroxy and halo radicals, K represents a radical selected from the class consisting of —BR, —BM and —NR$_2$, and M is a metal selected from the class consisting of alkali and alkaline earth metals.

U.S. Pat. No. 3,785,977 teaches the use of s-triazines as lubricant anti-oxidants having the formula

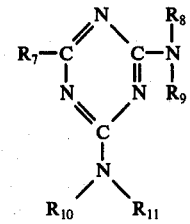

where R$_8$, R$_9$, R$_{10}$, R$_{11}$ are hydrogen, C$_1$ to C$_{20}$ hydrocarbyl or pyridyl, and R$_7$ is C$_1$ to C$_8$ hydrocarbyl, C$_1$ to C$_{20}$ hydrocarbylamine, pyridyl or pyridylamine.

It is an object of this invention to provide new lubricating oil compositions containing s-triazine derivatives.

It is further an object of this invention to provide lubricating oil copositions having improved dispersancy, extreme pressure or anti-oxidant properties.

SUMMARY OF THE INVENTION

This patent application relates to new lubricating oil compositions containing s-triazine derivatives. Disclosed are lubricating oil compositions containing from about 0.01 weight percent to about 5 weight percent of oil-soluble multifunctional additive having the general formula

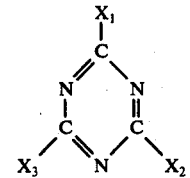

where
a. X$_1$ is —S—CS—OR, —S—CS—NR$_2$, —S—PS—(OR)$_2$, or —O—P(OR)$_2$, and X$_2$ and X$_3$ are chlorine, bromine, —S—CS—OR, —S—CS—NR$_2$, —S—P-S—(OR)$_2$, —OP(OR)$_2$, or R; or
b. X$_1$ is —S—CS—OR, —S—CS—NR$_2$—S—PS—(OR)$_2$, or —O—P—(OR)$_2$ and X$_2$ and X$_3$ are chlorine, bromine, —S—CS—OR, —S—CS—NR$_2$, —S—PS—(OR)$_2$, —O—P—(OR)$_2$ or HN—R'
where R comprises hydrocarbyl groups or chlorine, bromine or hydroxyl substituted hydrocarbyl; and R' comprises hydrocarbyl, or hydoxy, amine or amide substituted hydrocarbyl. Preferably, the compositions contain from about 0.5 to about 3.0 weight percent, more preferably about 0.5 to about 2.0 weight percent of the triazine derivatives. The compositions have improved extreme pressure, dispersancy or anti-oxidant properties.

R comprises hydrocarbyl such as alkyl, alkene, aryl or alkyl substituted aryl groups. R can be a straight chain or branched low molecular weight such as isobutyl or nonyl alkyls, and the like; intermedite molecular weight hydrocarbyl such as polypropylene or polybutene polymers having number average molecular weights from about 80 to about 5,000; high molecular weight hydrocarbyl such as polyolefins having a number average molecular weight up to about 100,000 or even higher; and others. R can be aryl such as a benzene ring or alkyl substituted aryl such as a mono or polyalkyl substituted benzene ring. R groups may be entirely hydrocarbon or substituted with chlorine, bromine or hydroxy groups. R can also be a mixture of various hydrocarbyl groups.

R' comprises hydrocarbyl, or hydroxy, amine or amide substituted hydrocarbyl. R' can be straight chain or branched hydrocarbyls of low, intermediate or high molecular weight as described above. R' can be aryl or alkyl substituted aryl. R' can contain unsaturation. R' can have amine substitution such as an ethylene polyamine (example — tetra ethylene pentanmine) or amide substitution by reacting amine substituents with acids having 1-36 carbon atoms, such as stearic, iso-stearic, and the like. R' can be hydroxy substituted such as N-hydroxyalkyl alkylene polyamines and the like.

Although R and R' can be any molecular weight, such compounds are often readily available containing one to thirty carbon atoms. R is preferably 1-8 carbon atoms and R' is preferably 10-20 carbon atoms.

The lubricating oils in which the compositions of this invention are useful as additives may be of synthetic, animal, vegetable, or mineral origin. Ordinarily mineral lubricating oils are preferred by reason of their availability, general excellence, and low cost. For certain applications, oils belonging to one of the other three groups may be preferred. For instance, synthetic polyester oils such as didodecyl adipate and di-2-ethylhexyl sebacate are often preferred as jet engine lubricants. Normally the lubricating oils preferred will be fluid oils, ranging in viscosity from about 40 Saybolt Univeral seconds at 100° F. to about 200 Saybolt Universal seconds at 210° F.

This invention contemplates also the presence of other additives in the lubricating compositions. Such additives include, for example, viscosity index improving agents, pour point depressing agents, anti-foam agents, extreme pressure agents, rust-inhibiting agents and oxidation and corrosin inhibiting agents.

S-triazine derivatives are often made through the reaction of cyanuric chloride or bromide with a metal salt of xanthates, metal —S—CS—NR$_2$; or dithiophosphates, metal —S—PS(OR)$_2$. Reaction of cyanuric chloride or bromide with amines is often conducted in the presence of a basic compound, such as triethyl amine or pyridine. For instance, reaction parameters of cyanuric chloride with phosphites can be found in Hewertson, W. et al., J. Chem. Soc. 1963, 1970 and Morrison, D. C., J. Org. Chem. 22 444 (1957); with xanthates in U.S. Pat. No. 3,261,834; with thiocarbamates in U.S. Pat. No. 3,139,350; with dithiophosphates in German Pat. No. 1,445,709; and in reaction with amines or polyamines in U.S. Pat. No. 3,309,345.

A number of s-triazine derivatives were synthesized as follows:

EXAMPLE 1

Tris(2,4,6-diethylphosphite)-s-triazine 0.4 mol triethylphosphite in 100 ml acetone was added portionwise with stirring at 5° C to 0.1 mole cyanuric chloride in 100 ml acetone. After addition the temperature was allowed to rise to room temperature. After 1 hr. the temperature was increased to 50° C and the reaction mixture stirred for 2 hrs. The solvent and unreacted phosphite was removed in vacuum at 50° C and 2 Torr.

| Elemental Analysis: | carbon | 36.8% |
|---|---|---|
| | hydrogen | 6.1 |
| | nitrogen | 8.8 |
| | phosphorus | 13.3 |
| | chlorine | 3.3 |

Bis(2,6-i-propyl xanthate)-4-diamyl dithiophosphate-s-triazine 0.1 ml Potassium diamyl dithiophosphate was added portionwise to 0.1 mol cyanuric chloride in 150 ml acetone at 10° C. After addition (1hr) the mixture was allowed to warm up to room temperature (0.5 hr) and then stirred for 2 hours at 40° C. The formed precipitate was removed and the solvent distilled off in vacuum. The reaction product was dissolved in 600 ml benzene, 0.2 mol potassium i-propylxanthate was added and the reaction mixture refluxed for 8 hrs. After filtering off the precipitate and distilling off the benzene, the product, an orange oil, was obtained.

| Elemental Analysis: | carbon | 41.1% |
|---|---|---|
| | hydrogen | 5.4 |
| | nitrogen | 8.2 |
| | phosphorus | 2.1 |
| | sulfur | 27.7 |

EXAMPLE 3

Tris(2,4,6-diamyl dithiophosphate)-s-triazine 0.15 mol potassium diamyl dithiophosphate was added at 10° C portionwise to 0.05 mol cyanuric chloride in acetone. The mixture was warmed up gradually to 40° C and removal of precipitate and solvent yielded the title product.

| Elemental Analysis: | carbon | 38.9% |
|---|---|---|
| | hydrogen | 5.4 |
| | nitrogen | 8.2 |
| | phosphorus | 2.1 |
| | sulfur | 27.7 |

EXAMPLE 3

Tris(2,4,6-diamyl dithiophosphate)-s-triazine 0.15 mol potassium diamyl dithiophosphate was added at 10° C portionwise to 0.05 mol cyanuric chloride in acetone. The mixture was warmed up gradually to 40° C and removal of precipitate and solvent yielded the title product.

| Elemental Analysis: | carbon | 38.9% |
|---|---|---|
| | hydrogen | 7.8 |
| | nitrogen | 5.2 |
| | phosphorus | 8.3 |
| | sulfur | 18.2 |

EXAMPLE 4

Bis(2,4-i-propyl xanthate)-6-diethylphosphite-s-triazine

Prepared in a manner similar to Example 2.

| Elemental Analysis: | carbon | 38.1% |
|---|---|---|
| | hydrogen | 5.4 |
| | nitrogen | 6.8 |
| | phosphorus | 6.2 |
| | sulfur | 21.0 |
| | chlorine | 2.1 |

EXAMPLE 5

Bis(2,4-dibtuyl thiocarbamate)-6-diethylphosphite-s-triazine

Prepared by reacting 0.2 mol zinc dibutyl-dithiocarbamate in 250 ml acetone with 0.1 m cyanuric chloride for 12 hrs at room temperature and 3 hrs at 50° C followed by reacting the product with 0.15 mol triethylphosphite at 50° C for 2 hrs.

| Elemental Analysis: | carbon | 44.0% |
|---|---|---|
| | hydrogen | 7.4 |
| | nitrogen | 5.9 |
| | phosphorus | 7.0 |
| | sulfur | 8.3 |
| | chlorine | 7.9 |

EXAMPLE 6

Bis(2,4-dibutyl thiocarbamate)-6-didecyldithiophosphate-s-triazine 18.4 g cyanuric chloride were reached with 47.3g zinc dibutyl dithiocarbomate in 250ml acetone for 2 hrs. at room temperature. 25g potassium didecyldithiophosphate were then added to the reaction mixture and the temperature raised to 50° C. After 3 hrs. at this temperature, the reaction mixture was filtered and the solvent removed in vacuo.

| Elemental Analysis: | carbon | 55.8% |
|---|---|---|
| | hydrogen | 8.9 |
| | nitrogen | 5.0 |
| | phosphorus | 3.2 |
| | sulfur | 12.9 |
| | chlorine | 2.0 |

EXAMPLE 7

Bis(2,4-diethylphosphite)-6-dithiophosphate-s-triazine

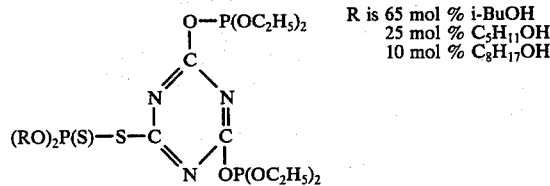

R is 65 mol % i-BuOH
25 mol % C$_5$H$_{11}$OH
10 mol % C$_8$H$_{17}$OH 15g of the potassium salt of a dithiophosphoric acid, prepared from P$_2$S$_5$ and a mixture of isobutanol, amyl and octyl alcohols, were added portionwise to 18.4g cyanuric chloride in 200 ml acetone at 10° C. After addition (1 hr) the reaction-mixture was allowed to warm up to room temperature (0.5 hr), the reaction was then continued for 2 hrs. at 40° C.

After removal of potassium chloride by filtration, 40g triethylphosphite were added portionwise at 15° C over a period of 0.5 hr.

After stirring for 1 hr. at this temperature, the reaction mixture was heated to 50° C for 2 hrs. The solvent was stripped off vacuo; unreacted triethylphosphite was removed at 90° C and 3 Torr.

| Elemental Analysis: | carbon | 41.9% |
|---|---|---|
| | hydrocarbon | 7.2 |
| | nitrogen | 7.1 |
| | phosphorus | 17.4 |
| | sulfur | 4.5 |
| | chlorine | 0.3 |

EXAMPLE 8

2-Diethylphosphite-4,6-bis(dithiophosphate)-s-triazine

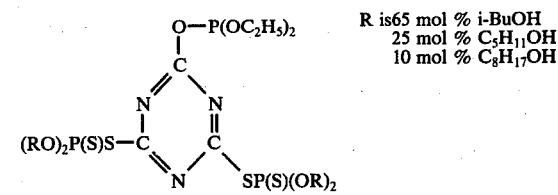

R is 65 mol % i-BuOH
25 mol % C$_5$H$_{11}$OH
10 mol % C$_8$H$_{17}$OH

Prepared by the same procedure as in Example 7.

| Elemental Analysis: | carbon | 41.8% |
|---|---|---|
| | hydrogen | 6.4 |
| | nitrogen | 8.8 |
| | phosphorus | 10.6 |
| | sulfur | 8.2 |

Mixture of bis(2,4-oleylamine)-6-i-propyl xanthate-s-triazine and 2-oleylamine-4,6-bis(i-propyl xanthate)-s-triazine 37g cyanuric chloride and 47.6g potassium isopropyl xanthate were refluxed in 400ml benzene for 6 hrs; 80g oleylamine was then added to the reaction mixture in the presence of 50ml triethylamine and the reaction mixture held at 60° C for 3 hrs. with stirring. Solids were removed by filtration. The low boiling material was stripped off by blowing with nitrogen.

| Elemental Analysis: | nitrogen | 11.0% |
|---|---|---|
| | sulfur | 18.2 |
| | chlorine | 1.9 |

Extreme pressure properties of lubricant compositions containing the disclosed triazine derivatives were measured using the Falex method (ASTM D 3233). The triazine derivatives were tested in the following oil formulation:
7% dispersant
5% viscosity index improver
1.9% methylene bis-dodecylphenol
40% 5W oil
balance 10 W oil
The results of such extreme pressure measurement

| Additive | Concentration % | Jaw Load at Failure (pounds) |
|---|---|---|
| None | — | 500 |
| Example 1 | 0.75 | 1900 |
| | 1.5 | 2350 |
| 2 | 0.75 | 1750 |
| | 1.5 | 1800 |
| 3 | 0.75 | 1550 |
| | 1.5 | 1650 |
| 4 | 0.75 | 1750 |
| | 1.5 | 1900 |
| 5 | 0.75 | 1300 |
| | 1.5 | 1700 |
| 6 | 0.75 | 1350 |
| | 1.5 | 1550 |
| 7 | 0.75 | 1606 |
| | 1.5 | 1750 |
| 8 | 0.75 | 1606 |
| | 1.5 | 2150 |
| 9 | 0.75 | 1500 |

-continued

| Additive | Concentration % | Jaw Load at Failure (pounds) |
|---|---|---|
|  | 1.5 | 1600 |
| 10 | 0.75 | 1500 |
|  | 1.5 | 1600 | show that the jaw load carrying capability and thus the extreme pressure capability of lubricating oils are improved by the incorporation of the various triazine derivatives.

Anti-oxidative properties of oil composition were measured by an oil thickening test. In this test 100 grams of test oil are oxidized at 350° F in an open oxidation tube, while being blown with 60 cc air/minute. Oxidation is catalyzed by the addition of 5% of a Ford VC drain oil Samples are taken periodically and their viscosity determined to give a viscosity-time curve. The time in hours for a four-fold increase in viscosity over the initial viscosity (4 Vo) is noted; a long 4 Vo indicates resistance to oil thickening by oxidation. Also, a sample of this oil after 47 hours of oxidation is run in the Spot Dispersancy Test which gives a measure of the oils ability to disperse sludge and varnish. In the Spot Dispersancy Test, 3-10 drops of oil are dropped onto a standard white blotter paper. After 24 hours, the diameter of the sludge spot and the oil spot are measured. Dispersancy is reflected by the ability of an oil to keep sludge in suspension. Thus, dispersancy will be reflected by the difference in diameters of the sludge and oil spots. A rating (SDT Rating) is given by the diameter of the sludge spot divided by the diameter of the oil spot, and multiplied by 100. A high numerical rating indicates good dispersancy. The test below were run on compositions containing triazine derivatives in the same oil formulation used previously:

| Additive | Concentration % | 4 Vo (hours) | SDT Rating |
|---|---|---|---|
| none | — | 22 | No dispersancy |
| Example 1 | 0.5 | 60 | 95 |
|  | 1.0 | 62 | 95 |
| 2 | 0.5 | 28 | No dispersancy |
|  | 1.0 | 35 | No dispersancy |
| 3 | 0.5 | 35 | 50 |
|  | 1.0 | 46 | 53 |
| 4 | 0.5 | 49 | 78 |
|  | 1.0 | 60 | 92 |
| 5 | 0.5 | 30 | No dispersancy |
|  | 1.0 | 34 | No dispersancy |
| 6 | 0.5 | 36 | 54 |
|  | 1.0 | 48 | 77 |
| 7 | 0.5 | 50 | 83 |
|  | 1.0 | 54 | 88 |
| 8 | 0.5 | 48 | 76 |
|  | 1.0 | 56 | 90 |

It can be seen that all the compositions tested containing triazine derivatives had improved anti-oxidant properties and a number of such composition also had improved dispersancy.

I claim:

1. A lubricating oil composition containing from about 0.01 weight percent to about 5 weight percent of one or more oil-soluble multifunctional additives having the general formula

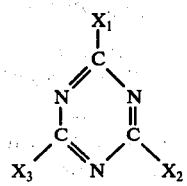

where
$X_1$ is —S—CS—OR, —S—CS—$NR_2$, —S—PS—$(OR)_2$, or —O—P—$(OR)_2$ and $X_2$ and $X_3$ are chlorine, bromine, —S—CS—OR, —S—CS—$NR_2$, —S—PS—$(OR)_2$, —O—P—$(OR)_2$, —HN—R'; or
where R comprises hydrocarbyl, chlorine substituted hydrocarbyl, bromine substituted hydrocarbyl or hydroxyl substituted hydrocarbyl; and R' comprises hydrocarbyl, hydroxy-substituted hydrocarbyl, amino substituted hydrocarbyl or amido substituted hydrocarbyl.

2. The composition of claim 1 wherein R comprises alkyl, aryl or alkyl substituted aryl, groups and chlorine, bromine or hydroxy substituted alkyl, aryl or alkyl substituted aryl groups, and R' comprises alkyl, alkene, aryl or alkyl substituted aryl groups and amino or amido substituted alkyl, alkene, aryl or alkyl substituted aryl groups.

3. The composition of claim 1 containing from about 0.05 weight percent to about 3 weight percent of said multifunctional additive.

4. The composition of claim 1 wherein R and R' contain one to thirty carbon atoms.

5. The composition of claim 4 wherein R is a $C_1$-$C_8$ hydrocarbon alkyl group.

6. The composition of claim 4 wherein R' is $C_{10}$-$C_{20}$ hydrocarbyl.

7. The composition of claim 1 containing from about 0.05 percent to about 2 percent of said oil-soluble multifunctional additive.

8. The composition of claim 1 wherein $X_1$, $X_2$ and $X_3$ are —S—PS—$(OR)_2$.

9. The composition of claim 8 wherein the multifunctional additive comprises Tris(2,4,6-diamyl dithiophosphate)-s-triazine.

10. The composition of claim 1 wherein $X_1$, $X_2$ and $X_3$ are —O—P—$(OR)_2$.

11. The composition of claim 10 wherein the multifunctional additives comprises Tris(2,5,6-diethylphosphite)-s-triazine.

12. The composition of claim 1 wherein $X_1$ is —S—P-S—$(OR)_2$ and $X_2$ and $X_3$ are —C—CS—OR.

13. The composition of claim 12 wherein the multifunctional additive comprises Bis(2,6-i-propyl xanthate)-4-diamyl dithiophosphate-s-triazine.

14. The composition of claim 1 wherein $X_1$ is —OP-$(OR)_2$ and $X_2$ and $X_3$ are —S—CS—OR.

15. The composition of claim 14 wherein the multifunctional additive comprises Bis(2,4-i-propyl xanthate)-6-diethylphosphite)-s-triazine.

16. The composition of claim 1 wherein $X_1$ is —O-—P—$(OR)_2$ and $X_2$ and $X_3$ are —S—CS—$NR_2$.

17. The composition of claim 16 wherein the multifunctional additive comprises Bis(2,4-dibutyl thiocarbamate)-6-diethylphosphite-s-triazine.

18. The composition of claim 1 wherein $X_1$ is —S—P-S—$(OR)_2$ and $X_2$ and $X_3$ are —S—CS—$NR_2$.

19. The composition of claim 18 wherein the multifunctional additive comprises Bis(2,4-dibutyl thiocarbamate)-6-didecyldithiophophate-s-triazine.

20. The composition of claim 1 wherein $X_1$ is —S—P—S—$(OR)_2$ and $X_2$ and $X_3$ are —O—P—$(OR)_2$.

21. The composition of claim 20 wherein the multifunctional additive comprises Bis(2,4-diethylphosphite)-6-dithiophosphate-s-triazine.

22. The composition of claim 1 wherein $X_1$ is —O—P—$(OR)_2$ and $X_2$ and $X_3$ are —S—PS—$(OR)_2$.

23. The composition of claim 22 wherein the multifunctional additive comprises 2-diethylphosphite-4,6-bis(dithiophosphate)-s-triazine.

24. The composition of claim 1 containing a first multifunctional additive wherein $X_1$ is —S—CS—OR and $X_2$ and $X_3$ are $H_2N$—R' and a second multifunctional additive wherein $X_1$ and $X_2$ are —S—CS—OR and $X_3$ is $H_2N$—R'.

25. The composition of claim 24 wherein the multifunctional additive comprises a mixture of bis(2,4-oleylamine)-6-i-propyl xanthate-s-triazine and 2-oleylamine-4,6-bis(i-propyl xanthate)-s-triazine.

26. The composition of claim 1 wherein $X_1$, $X_2$ and $X_3$ are chlorine, bromine, —S—CS—OR, —S—PS—$(OR)_2$, —O—P—$(OR)_2$ or mixtures thereof, where R and R' are a $C_1$-$C_{30}$ hydrocarbyl radicals.

* * * * *

UNITED STATES PATENT OFFICE
CERTIFICATE OF CORRECTION

Patent No. 4,038,197                    Dated  July 26, 1977

Inventor(s) Caspari, Gunter

It is certified that error appears in the above-identified patent and that said Letters Patent are hereby corrected as shown below:

| | | | |
|---|---|---|---|
| Col. 2, | line | 19 | "copositions" should be -- compositions |
| " 2 | " | 43 | "-S-CS-NR$_2$-S-PS-" should be -S-CS-NR$_2$, -S-PS- |
| " 2, | " | 45 | "or HN-R'" should be -- or -HN-R' |
| " 2, | " | 48 | "hydroxyl" should be -- hydroxy |
| " 2, | " | 59 | "intermedite" should be -- intermediate |
| " 3, | " | 36 | "corrosin" should be -- corrosion |
| " 4, | " | 5 | "Example 2" is missing |
| " 5, | " | 23 | "were reached" should be--were reacted |
| " 6, | " | 25 | "Example 9" is missing |
| " 8, | " | 21 | "wherein" should be -- where |
| " 8, | " | 22 | "substituted alkyl, aryl" should be -- substituted alkyl aryl |
| " 8, | " | 25 | "groups and amino or amido" should be -- groups and hydroxy, amino or amido |

Col. 4, lines 27 through 40, omit the first Example 3.

*Signed and Sealed this*

*Twentieth* Day of *December 1977*

[SEAL]

Attest:

RUTH C. MASON
*Attesting Officer*

LUTRELLE F. PARKER
*Acting Commissioner of Patents and Trademarks*